United States Patent

Cutler et al.

[11] Patent Number: 6,117,820
[45] Date of Patent: Sep. 12, 2000

[54] AGROCHEMICAL FORMULATION

[75] Inventors: Julia Lynne Cutler; Michael John Bean, both of Bracknell, United Kingdom

[73] Assignee: ZENECA Limited, United Kingdom

[21] Appl. No.: 09/132,294

[22] Filed: Aug. 11, 1998

[30] Foreign Application Priority Data

Aug. 27, 1997 [GB] United Kingdom ............... 9718139

[51] Int. Cl.$^7$ ................................ A01N 25/30
[52] U.S. Cl. ............... 504/206; 504/222; 504/250; 504/333; 504/362; 514/975
[58] Field of Search .................. 504/116, 206, 504/222, 250, 333, 362; 514/975

[56] References Cited

U.S. PATENT DOCUMENTS

| | | | |
|---|---|---|---|
| 5,612,285 | 3/1997 | Arnold | 504/206 |
| 5,888,934 | 3/1999 | Townson et al. | 504/206 |

FOREIGN PATENT DOCUMENTS

| | | |
|---|---|---|
| 0 388 239 A1 | 9/1990 | European Pat. Off. |
| 0 388 810 A2 | 9/1990 | European Pat. Off. |
| 0 498 231 A1 | 8/1992 | European Pat. Off. |
| 94/12259 | 6/1994 | WIPO . |
| 95/00612 | 1/1995 | WIPO . |
| 95/16351 | 6/1995 | WIPO . |
| 96/00010 | 1/1996 | WIPO . |
| 97123131 | 7/1997 | WIPO . |

OTHER PUBLICATIONS

G. Platz, et al., *Phase behaviour of alkyl polyglucocides in combination with fatty alcohols and alkyl sulphates*, Colloids and Surfaces, 88 at 113–122 (1994).

*Primary Examiner*—S. Mark Clardy
*Attorney, Agent, or Firm*—David P. LeCoy

[57] ABSTRACT

An aqueous agrochemical concentrate formulation comprises a) an agrochemical electrolyte such as salts of glyphosate, fomesafen, glufosinate, paraquat or bentazone, b) an alkoxylated adjuvant, c) an alkylglycoside and d) a co-surfactant which interacts with the alkylglycoside to form a structured aqueous system. Preferred co-surfactants are:- (i) a linear or branched chain aliphatic or aromatic alcohol, (ii) an alcohol or ester or alkyl phenol alkoxylate having a degree of alkoxylation lower than that of the alkoxylated adjuvant present in the formulation as component (b), (iii) a glyceryl alkyl or alkenyl ester and (iv) a sorbitan alkyl or alkenyl ester. The alkyl glycoside and the co-surfactant interact to provide a structured aqueous system such that if the critical concentrations are exceeded and one or more components (normally the alkoxylated adjuvant) can no longer be maintained in a single-phase aqueous system, the second phase forms a stable dispersion (normally a liquid phase dispersion) which is supported within the structured aqueous system.

13 Claims, No Drawings

AGROCHEMICAL FORMULATION

The present invention relates to agrochemical formulations and in particular to aqueous formulations containing high concentrations of agrochemical electrolytes.

An agrochemical is generally used with an adjuvant or specific combinations of adjuvants to provide optimum biological activity. Much has been published on the selection of adjuvants and specific combinations of adjuvants have been designed to achieve particular effects with individual agrochemicals and classes of agrochemical. In commercial practice it is often desired to minimise transportation and storage costs by using a formulation in which the concentration of the active agrochemical in the formulation is as high as is practicable and in which the desired adjuvants are "built-in" to the formulation as opposed to being separately tank-mixed. Appropriate adjuvants are selected to provide formulation stability in the "built-in" formulation, as well as delivering the required biological effect. The higher the concentration of the active agrochemical and its associated adjuvants however, the greater is the probability that the stability of the formulation may be disturbed and one or more component separates out, for example as a discrete phase. In general, the separation of a discrete phase from an agrochemical is highly undesirable, particularly when the formulation is sold in bulk containers. In these circumstances it is virtually impossible to re-homogenize the formulation and to achieve even distribution of the components on dilution and spraying. Furthermore, the formulation must be stable in respect of storage for prolonged periods in both hot and cold climates. These factors all present formidable problems to the formulator.

One widely used and highly effective class of adjuvants is that obtained by alkoxylation of a nonionic or cationic substrate. For example, Wyrril and Burnside (Weed Science 1977 Vol 25 275–287) have shown that ethoxylated alcohols, esters and amines can be used to improve the biological performance of glyphosate. Particular problems can arise when alkoxylated adjuvants are combined with agrochernical electrolytes since all surfactants of the alkoxylate type undergo phase separation at a particular electrolyte concentration and temperature. One solution to this problem is to add a co-surfactant, solubiliser or hydrotrope that raises the cloud point of the alkoxylate, i.e., increases the electrolyte concentration or the temperature at which the phase separation occurs. Some success can be achieved in this area, for example, by adding a cationic surfactant to an alcohol ethoxylate, the alcohol ethoxylate can be formulated at a higher electrolyte concentration than would otherwise be possible. However this approach is of limited success in some instances, for example when high concentrations of the agrochemical electrolyte and the alkoxylate are required or if the formulation is required to be stable over a broad temperature range. Above a certain concentration of agrochemical electrolyte, unstable formulations would be produced at all practical temperatures.

We have now found that it is possible to provide specific combinations of formulants which enable an alkoxylated adjuvant to be formulated in an electrolyte concentration at which the adjuvant would normally undergo unacceptable phase separation.

Thus according to the present invention there is provided an aqueous agrochemical concentrate formulation comprising a) an agrochemical electrolyte
b) an alkoxylated adjuvant
c) an alkylglycoside
d) a co-surfactant which interacts with the alkylglycoside to form a structured aqueous system.

While the scope of the present invention is not limited by any one particular theory as to the function of the components of the formulation, it is believed that the components, (and in particular the alkyl glycoside and the co-surfactant) interact to provide a structured aqueous system. Thus even if the critical concentrations are exceeded such that one or more components (normally the alkoxylated adjuvant) can no longer be maintained in a single-phase aqueous system, the second phase forms a stable dispersion (normally a liquid phase dispersion) which is supported within the structured aqueous system. Thus in contrast to prior art systems in which attempts have been made to overcome separation problems by adding still further "solubilising" components to maintain a single phase system, it is not essential that the formulation of the present invention is maintained as a single phase system. It is believed that the present invention provides a structured aqueous system, even in the presence of a second dispersed phase, such that a substantially homogeneous dispersion gives a uniform concentration in respect of all the components within the formulation.

As examples of the co-surfactant which interacts with the alkylglycoside to form a structured aqueous system there may be mentioned compounds having a hydrophobic group in combination with a relatively small hydrophilic group for example:

i) a linear or branched chain aliphatic or aromatic alcohol or ii) an alcohol or ester or alkyl phenol alkoxylate having a degree of alkoxylation lower than that of the alkoxylated adjuvant present in the formulation as component (b) or iii) a glyceryl alkyl or alkenyl ester or (iv) a sorbitan alkyl or alkenyl ester.

As used herein, the term alkyl includes a linear or branched chain alkyl group and the term alkyl alcohol includes a linear or branched primary, secondary or tertiary alcohol. A linear or branched primary or secondary alkyl alcohol is generally preferred. As used herein, the term alkenyl includes a linear or branched alkenyl group and the term alkenyl alcohol includes a linear or branched primary, secondary or tertiary alcohol. A linear or branched primary or secondary alkenyl alcohol is generally preferred.

The linear or branched chain alcohol (i) is preferably a primary or secondary, linear or branched alkyl or alkenyl alcohol containing from 5 to 20 carbon atoms or is an alkyl-or alkenyl- substituted aromatic alcohol containing from 5 to 20 alkyl linear or branched carbon atoms, for example an alkylphenol containing from 5 to 20 alkyl carbon atoms. More preferably the alcohol is an alkyl alcohol containing from 5 to 12 carbon atoms or an alkenyl alcohol containing about 18 carbon atoms. As specific examples of suitable alcohols there may be mentioned pentanol, hexanol, octanol, octan-2-ol, decanol and their branched chain or mixture of branched chain equivalents and oleyl alcohol. As a specific example of a branched chain alcohol there may be mentioned 2-ethyl-1-hexanol. Although it is believed that the structuring of the aqueous phase is more than a mere viscosity effect, we have found that the viscosity of the formulation depends on the choice of alcohol. In general an excessively viscous formulation is less commercially desirable since it can be more difficult to handle a viscous formulation. We have found in particular that a branched alcohol such as 2-ethylhexanol gives effective dispersion through structuring of the aqueous phase while providing a relatively low-viscosity formulation even at low ambient temperatures.

The alcohol, ester or alkyl phenol alkoxylate having a degree of alkoxylation lower than that of the alkoxylated adjuvant present in the formulation as component (b) (co-surfactant (ii)) preferably has an alkoxide content of from 1 to 5, and more preferably from 1 to 3 $C_2$–$C_4$ alkoxy groups. The co-surfactant (ii) is preferably an alkoxylated $C_8$–$C_{22}$ alcohol, an alkoxylated $C_8$–$C_{22}$ alkyl phenol or an alkoxylated $C_8$–$C_{22}$ carboxylic acid each containing from 1–3 ethoxy groups. A suitable example is SYNPERONIC L2 which is based on lauryl alcohol with a mean ethylene oxide content of 2. A suitable example of the alkyl phenol alkoxylate is SYNPERONIC OP3 which is an ethoxylated octyl phenol with a mean degree of ethoxylation of 3.

As used herein (both generally and with specific reference to the alkoxylated adjuvant (b) and the alcohol or ester or alkyl phenol alkoxylate (ii)), the term "alkoxylated" includes both those compounds in which the alkoxy chain terminates in a hydroxyl group and those in which the alkoxy chain terminates in an alkyl group, such as a methyl group. Preferred alkoxyl groups are ethoxy or propoxy, and a mixture of alkoxy groups, for example a mixture of ethoxy and propoxy groups, may be present in the same alkoxylated molecule if desired.

The glyceryl alkyl or alkenyl ester (co-surfactant (iii)) is preferably a monoester of a $C_8$–$C_{22}$ carboxylic acid with glycerol. A suitable example is CITHROL GML which is glyceryl monolaurate.

The sorbitan alkyl or alkenyl ester preferably contains from 8 to 22 carbon atoms in the ester group, an especially suitable sorbitan ester is a sorbitan monolaurate such as that available under the trade name SPAN 20.

The agrochemical electrolyte may be an active agrochemical or an agrochemical enhancer such as ammonium sulphate or any other ionic species added to an agrochemical formulation. Suitable agrochemical actives which are agrochemical electrolytes are glyphosate (N-phosphonomethylglycine), which is commonly used in the form of its water-soluble salts such as trimethylsulphonium, isopropylamine, sodium, or ammonium salts, fomesafen which is commonly used in the form of its water-soluble sodium salt, glufosinate which is commonly used in the form of its water-soluble ammonium salt, paraquat dichloride and bentazone which is commonly used in the form of its water-soluble sodium salt. The use of an agrochemical enhancer or other additive which is itself an electrolyte may still further enhance the ionic strength of the composition, thereby increasing the potential stability problems. Thus, for example, glyphosate salts are commonly formulated or tank-mixed with ammonium sulphate as an activity enhancer, while magnesium sulphate may be added to paraquat as a purgative as disclosed for example in EP 0467529.

The alkoxylated adjuvant (b) contains one or more $C_1$–$C_4$ alkoxy groups, for example one or more propoxy or ethoxy groups or a mixture thereof. The alkoxylated adjuvant (b) preferably contains from 6 to 50 alkoxy groups, for example from 7 to 20 alkoxy groups except when it is a block copolymer as described below.

Suitable alkoxylated non-ionic adjuvants include ethoxylated primary or secondary linear or branched alcohols preferably containing an average of from 8 to 22 carbon atoms in the (linear or branched) alkyl moiety, ethoxylated carboxylic acids preferably containing an average of from 8 to 22 carbon atoms in the (linear or branched) alkyl moiety, ethoxylated alkyl aryls such as ethoxylated alkyl phenols wherein the (linear or branched) alkyl group preferably contains an average of from 5 to 20 carbon atoms, ethoxylated sorbitan esters wherein the ester group contains from 8 to 22 carbon atoms, ethoxylated acetylenic diols preferably containing from 8 to 22 carbon atoms in the (linear or branched) alkyl moiety, ethoxylated trisiloxanes, ethoxylated amides and the propoxylated or ethoxylated and propoxylated analogues of all the aforesaid ethoxylated non-ionic adjuvants. As used herein, the term "alkoxylated adjuvant" includes block copolymers containing alkoxy groups, such as block copolymers of ethylene oxide and propylene oxide and block copolymers obtained by polycondensation of ethylene oxide and propylene oxide on ethylenediamine. Block copolymers preferably contain from 30% by weight to 80% by weight of ethylene oxide.

Preferred alkoxylated non-ionic adjuvants have a HLB value in the range 10–20.

The alkoxylated non-ionic adjuvant may be a water miscible or water immiscible liquid or a water-soluble or water-insoluble solid. Preferably the alkoxylated non-ionic adjuvant is a liquid or a water-soluble solid.

A number of suitable ethoxylated alcohols are commercially available including for example the SYNPERONIC A series having a range of ethylene oxide contents (indicated by the number after the "A") and based on a $C_{13}$–$C_{15}$ alcohol containing about 50% by weight linear alcohol, the remainder being mainly mono-branched; BRIJ 96 and 98 based on an unsaturated $C_{18}$ linear alcohol and having a mean ethylene oxide content of 10 and 20 respectively; MERGITAL LM 11 based on $C_8$–$C_{14}$ alcohol having a mean ethylene oxide content of 11; MERGITAL LM 17 based on $C_{10}$–$C_{14}$ alcohol having a mean ethylene oxide content of 17 and RHODASURF TR/15 based on a branched $C_{13}$ alcohol having a mean degree of ethoxylation of 15. An example of a suitable secondary alcohol ethoxylate is Tergitol 15-S-9, based on a mixture of $C_{11}$–$C_{15}$ linear secondary alcohols having a mean ethylene oxide content of 9. An example of a suitable ethoxylated carboxylic acid is Cithrol 6ML which is ethoxylated laurate with a mean ethylene oxide content of 12. An example of a suitable ethoxylated alkyl phenol is Synperonic NP13 based on nonyl phenol with a mean ethylene oxide content of 13. An example of a suitable ethoxylated sorbitan ester is Tween 20 which is ethoxylated sorbitan monolaurate with a mean ethylene oxide content of 20. An example of a suitable ethoxylated acetylenic diol is Surfynol 465 which is based on tetramethyldecynediol with a mean ethylene oxide content of 10. An example of a suitable ethoxylated trisiloxane is Silwet L77 which is a methyl capped ethoxylated trisiloxane with a mean ethylene oxide content of 8. Examples of suitable block copolymers of ethylene oxide and propylene oxide are Synperonic PE L44 and Synperonic PE P85. Synperonic PE L44 has a molecular weight of 2200 and contains 40 weight % ethylene oxide; Synperonic PE P85 has a molecular weight of 4650 and contains 50 weight % ethylene oxide.

Typical of alkoxylated cationic adjuvants are alkoxylated and preferably ethoxylated amines and quaternary ammonium salts. Preferred cationic adjuvants contain a mean degree of ethoxylation of 6–20 moles.

The alkylglycoside for use in the present invention may be obtained by the reaction of alkanols with glucose or other mono- or di- or polysaccharides. As used herein the term "alkylglycoside" includes an alkylmonoglycoside and an alkylpolyglycoside. Preferred alkylglycosides for use in the present invention are alkylglucosides obtained by the reaction of glucose with a straight or branched chain alkanol or mixture of alkanols, for example a mixture of alkanols containing 7 to 18, preferably 7 to 16 carbon atoms, for example 8 to 10 carbon atoms. The number of glycose groups per alkyl group in the molecule may vary and alkyl mono- or di- or polyglucose or saccharide derivatives are possible. Commercial alkylpolyglucosides usually contain a mixture of derivatives having an average number of glycose groups per alkyl group. Thus alkylglycosides have the general formula (I)

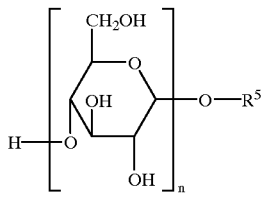

(I)

wherein n is the degree of polymerisation and is typically within the range from 1 to 3, for example from 1 to 2, and $R^5$ is a branched or straight chain alkyl group having from 4 to 18 carbon atoms or a mixture of alkyl groups having an average value within the given range. Typical of alkylglycosides is the product commercially available under the trade names AL2042 (Imperial Chemical Industries PLC) and AGRIMUL PG2067 (Henkel Corp) wherein n is an average of 1.7 and $R^5$ is a mixture of octyl (45%) and decyl (55%), the product commercially available under the trade name AGRIMUL PG2069 (Henkel Corp) wherein n is an average of 1.6 and $R^5$ is a mixture of nonyl (20%), decyl (40%) and undecyl (40%) and the product commercially available under the trade name BEROL AG6202 (Akzo Nobel) which is 2-ethyl-1-hexylglycoside.

As indicated previously, the agrochemical formulations of the present invention are preferably stable at relatively high ambient temperatures. It has been found that enhanced high temperature stability may be obtained by the inclusion of a minor proportion of an ionic surfactant (component e) which is different from the ethoxylated adjuvant (component b). It is believed that the presence of a minor proportion of an ionic surfactant in the formulation increases the amount of structuring that occurs, particularly at high temperatures. The addition of an ionic surfactant therefore offers another advantage, in that lower concentrations of the alkylglycoside and co-surfactant (d) can be used to produce stable formulations.

It is especially preferred to use an ethoxylated adjuvant (component b) which is an ethoxylated non-ionic surfactant in combination with an ionic surfactant (component e).

A wide range of suitable ionic surfactants (component e) will occur to those skilled in the art and those which have been found to enhance stability include cationic, anionic and amphoteric surfactants. Particularly suitable cationic surfactants include optionally ethoxylated amines, quaternary ammonium salts and amine oxides having at least one long chain (linear or branched) alkyl or alkenyl or alkyl aryl substituent containing from 8 to 20 carbon atoms in the alkyl or alkenyl group and a preferred mean ethylene oxide content of from 0 to 20, even more preferably from 0 to 5. Particularly suitable anionic surfactants include alkyl sulphates, alkyl carboxylates, alkyl sulphosuccinates, alkyl phosphates and alkylbenzene sulphonates and their derivatives having at least one long chain alkyl or alkenyl substituent containing from 8 to 20 carbon atoms. In some instances the additional ionic surfactant may even provide an increase in the activity of the composition.

Thus, for example, when the agrochemical electrolyte is glyphosate and is used with a non-ionic ethoxylated adjuvant as component (b), especially preferred additional surfactants (component e) are cationic surfactants such as ethoxylated amines and optionally ethoxylated quaternary ammonium salts. Examples of suitable additional cationic surfactants include hexadecyl trimethyl ammonium chloride, coco trimethyl ammonium chloride and N-methyl cocoammonium chloride having a mean ethylene oxide content of 2.

As noted above, the advantages of the formulation of the present invention are fully realized at high concentrations of the agrochemical electrolyte and the alkoxylated adjuvant such that, in the absence of the co-surfactant which interacts with the alkylglycoside to form a structured aqueous system (component d), one or more component (usually the alkoxylated adjuvant) undergoes inhomogeneous phase separation, thereby destroying the homogeneity of the concentration of the components within the formulation. In particular, the concentration of the agrochemical electrolyte may be at the higher end of that found in practice for formulations of the agrochemical electrolyte. Such typical concentrations will be known to those skilled in the art or may be determined by routine experimentation in respect of the agrochemical electrolyte concerned.

The agrochemical glyphosate is especially suitable for formulation according to the present invention. Thus for example the present invention provides formulations of glyphosate wherein the concentration of glyphosate salt (expressed as glyphosate acid) is greater than 240 g/l and more particularly greater than 300 g/l, for example about 330 g/l or more. The formulation of the present invention may contain both relatively high concentrations of glyphosate salt up to about 330 g/l or more glyphosate salt (expressed as glyphosate acid) and up to about 120 g/l or more of alkoxylated adjuvant.

The proportion of alkoxylated adjuvant in the formulation of the invention is preferably from 8 parts by weight alkoxylated adjuvant per 1 part by weight alkyl glycoside to 1 part by weight alkoxylated adjuvant per 8 parts by weight alkylglycoside, for example 5 parts by weight alkoxylated adjuvant per 1 part by weight alkyl glycoside to 1 part by weight alkoxylated adjuvant per 8 parts by weight alkylglycoside and most preferably from 1 part by weight alkoxylated adjuvant per 0.5 parts by weight alkylglycoside to 1 part by weight alkoxylated adjuvant to 8 parts by weight alkylglycoside. An especially preferred composition contains about equal proportions by weight of alkylglycoside and alkoxylated adjuvant.

The co-surfactant (component d) present in the formulation is preferably from 0.1 parts by weight to 1 part by weight per 1 part by weight of alkylglycoside and most preferably from 0.2 parts by weight to 0.8 parts by weight of co-surfactant per 1 part by weight of alkyglycoside.

The proportion of additional ionic surfactant (component e) is preferably from 0 to 1 part by weight per 1 part by weight alkylglycoside and most preferably from 0.1 parts by weight to 0.3 parts by weight ionic surfactant per 1 part alkylglycoside.

The proportion by weight of the total adjuvant system (alkyl polyglycoside, alkoxylated adjuvant and ionic surfactant, if used) to the agrochemical electrolyte is preferably from 2:1 to 1:5 and especially from 1:1 to 1:4.

Other additives, humectants or additional adjuvants may also be present in compositions of the present invention. Examples include anti-freeze agents such as ethylene glycol, urea and propylene glycol; dyes; polymers; dispersants;

rheological agents; and anti-foam agents such as silicone based agents. If any such additional component, whether a liquid or an insoluble solid, itself has a tendency to phase separate or settle from the composition, the structured phase provided by the present invention will additionally serve to keep such additional component homogeneously distributed throughout the formulation.

Compositions of the present invention provide adjuvant enhancement for the active agrochemical concerned or increase the effectiveness of the adjuvant if the agrochemical electrolyte is an agrochemical enhancer such as ammonium sulphate. Thus formulations of the invention wherein the agrochemical electrolyte is a herbicide, and in particular when the herbicide is glyphosate, are active against a broad range of weed species including monocotyledonous and dicotyledonous species.

Thus according to a further aspect of the present invention wherein the agrochemical electrolyte is a herbicide, there is provided a process of severely damaging or killing unwanted plants which comprises applying to the plants a herbicidally effective amount of a composition of the present invention.

The rate of application of the composition of the invention will depend on a number of factors including, for example, the active ingredients chosen for use, the identity of the plants whose growth is to be inhibited and the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may also comprise one or more additional compounds which possess biological activity, for example herbicides, fungicides, insecticides (optionally with an insecticide synergist) and plant growth regulators.

We have found that the development of a structured aqueous phase and a homogeneous dispersion which gives a uniform distribution in respect of all the components within the formulation, is not crucially dependent on the method of preparation of the formulation. Typically, the agrochemical electrolyte is dissolved in the desired quantity of water and the alkylglycoside and alkoxylated adjuvant are added with warming and stirring of the resultant solution. Any further surfactant is then added followed by the alcohol and any additional components such as an anti-foam. As indicated previously, it is not necessary that all components of the formulation remain in solution as a single phase, since the structuring provided by the formulation of the invention ensures that all components remain substantially uniformly distributed throughout the formulation.

Thus according to a further aspect of the present invention there is provided a process for the preparation of a composition according to the present invention wherein the agrochemical electrolyte, the alkylglycoside and the alkoxylated adjuvant are dissolved or dispersed in water with the further ionic surfactant, if used, and thereafter the co-surfactant is added and interacts with the alkylglycoside to form a structured system.

In general, we have not encountered significant problems in diluting the formulation of the present invention ready for agrochemical use, although excessively viscous or excessively structured compositions may require care to ensure that the concentrate has been effectively dissolved in the water of dilution before use.

The invention is illustrated by the following Examples in which all parts and percentages are by weight unless otherwise stated. The description of commercially available surfactants has been given above.

EXAMPLES 1 TO 10

Compositions according the invention were prepared according to the following general procedure:

The trimethylsulphonium salt of glyphosate (component a), alkylglycoside (component c - AGRIMUL PG2067) and water were combined to form a solution. This solution was warmed to about 40° C. whilst stirring at 300–500 rpm with a Heidolp PZ R50 mixer, typically fitted with a four bladed stirrer. A non-ionic ethoxylated adjuvant (component b), which was warmed until fluid, was added and the mixture stirred for five minutes, after which the heating was discontinued. A cationic surfactant (component e) was then added and mixed for about five minutes. Finally an alcohol (component d) was added and stirred for fifteen minutes with the stirrer speed increased to 500–750 rpm. The sample was left to stand at room temperature to cool.

The following compositions all formed clear or slightly turbid formulations with no visible sign of inhomogeneous phase separation on storage at ambient temperature and 54° C. for one month.

| Example 1 | | Example 2 | |
|---|---|---|---|
| Glyphosate trimesium | 480 g/l | Glyphosate trimesium | 480 g/l |
| AGRIMUL PG2067* | 110 g/l | AGRIMUL PG2067 | 110 g/l |
| SYNPERONIC A16* | 110 g/l | SYNPERONIC A16 | 110 g/l |
| ARQUAD 16-29* | 69 g/l | ETHOMEEN T25* | 20 g/l |
| Octanol | 50 g/l | Octanol | 60 g/l |
| Water | to 1 liter | Water | to 1 liter |

*AGRIMUL PG2067 is a 70% w/w solution of alkylpolyglycoside of formula (I) above wherein n is an average of 1.7 and $R^5$ is a mixture of octyl (45%) and decyl (55%).
AGRIMUL is a trademark of Henkel.
SYNPERONIC A16 is a blend of the ethoxylated alcohol SYNPERONIC A11 which has a mean ethylene oxide content of 11 with SYNPERONIC A20 (which has a mean ethylene oxide content of 20) in the ratio 3 to 2.
SYNPERONIC is a trademark of Imperial Chemical Industries.
ARQUAD 16-29 is a 29% by weight solution of hexadecyl trimethyl ammonium chloride in water. ARQUAD is a trademark of Akzo Nobel.
ETHOMEEN T25 is an ethyoxylated tallowamine having 15 moles of ethylene oxide per mole of tallowamine. ETHOMEEN is a trademark of Akzo Nobel.

| Example 3 | | Example 4 | |
|---|---|---|---|
| Glyphosate trimesium | 480 g/l | Glyphosate trimesium | 480 g/l |
| AGRIMUL PG2067 | 110 g/l | AGRIMUL PG2067 | 110 g/l |
| SYNPERONIC A16 | 110 g/l | SYNPERONIC A11 | 110 g/l |
| ETHOMEEN C25 | 20 g/l | ARQUAD 16-29 | 69 g/l |
| Octanol | 60 g/l | 2-Ethylhexanol | 60 g/l |
| Water | to 1 liter | Water | to 1 liter |

| Example 5 | | Example 6 | |
|---|---|---|---|
| Glyphosate trimesium | 480 g/l | Glyphosate trimesium | 480 g/l |
| AGRIMUL PG2067 | 110 g/l | AGRIMUL PG2067 | 110 g/l |
| SYNPERONIC A16 | 110 g/l | SYNPERONIC A16 | 110 g/l |
| ARQUAD C35* | 57 g/l | ARQUAD 16-29 | 69 g/l |
| 2-Ethylhexanol | 50 g/l | 2-Ethylhexanol | 60 g/l |
| Water | to 1 liter | Water | to 1 liter |

*ARQUAD C35 is a 35% by weight solution of cocotrimethylammonium chloride in water.

| Example 7          |           | Example 8          |           |
|--------------------|-----------|--------------------|-----------|
| Glyphosate trimesium | 480 g/l | Glyphosate trimesium | 480 g/l |
| AGRIMUL PG2067     | 110 g/l   | AGRIMUL PG2067     | 110 g/l   |
| RHODASURF TR/15*   | 110 g/l   | RHODASURF TR/15*   | 110 g/l   |
| ARQUAD 16-29       | 69 g/l    | ARQUAD 16-29       | 69 g/l    |
| Octanol            | 60 g/l    | 2-Ethylhexanol     | 60 g/l    |
| Water              | to 1 liter | Water             | to 1 liter |

*RHODASURF TR/15 is a polyoxyethylene tridecylalcohol having a mean degree of ethoxylation of 15. RHODASURF is a trademark of Rhone Poulenc.

| Example 9          |           | Example 10         |           |
|--------------------|-----------|--------------------|-----------|
| Glyphosate trimesium | 480 g/l | Glyphosate trimesium | 480 g/l |
| AGRIMUL PG2067     | 110 g/l   | AGRIMUL PG2067     | 115 g/l   |
| MERGITAL LM17*     | 110 g/l   | MERGITAL LM11*     | 115 g/l   |
| ETHOQUAD C12*      | 27 g/l    | ARQUAD 16-29       | 34 g/l    |
| 2-Ethylhexanol     | 60 g/l    | 2-Ethylhexanol     | 50 g/l    |
| Water              | to 1 liter | Water             | to 1 liter |

*ETHOQUAD C12 is a 75% by weight solution in 2-propanol of ethoxylated coco methyl ammonium chloride having a degree of ethoxylation of 2. ETHOQUAD is a trademark of Akzo Nobel.
MERGITAL LM17 is an ethoxylated $C_{12}$–$C_{16}$ alcohol having a mean degree of ethoxylation of 17. MERGITAL is a trademark of Sidobre Sinnova.
MERGITAL LM11 is ethoxylated $C_{12}$–$C_{16}$ alcohol having a mean degree of ethoxylation of 11.

EXAMPLE 10A

The compositions of Examples 1 to 10 were stored at 54° C. for 4 weeks and were assessed for homogeneity after this period. The assessment for homogeneity involved the extraction of an aliquot sample from the top and the bottom respectively of the undisturbed sample after storage. The FT-IR (Fourier Transform Infra Red) spectrum of each aliquot was recorded and substantial identity of the spectrum of the top and bottom aliquot was found for the compositions of all Examples except Examples 2 and 3. In contrast, the compositions of Examples 2 and 3 containing ETHOMEEN T25 and ETHOMEEN C25 respectively showed slight displacement between the FT-IR spectrum of the top and bottom aliquot respectively and it is concluded that these cationic surfactants (component e) are less effective in preserving high-temperature stability than cationic surfactants (component e) having the preferred ethylene oxide content of from 0 to 5

COMPARISON 1

Compositions corresponding to those of Examples 4, 9 and 10 were prepared without the addition of the alcohol component. All three compositions separated out into discrete layers after standing at room temperature for a few hours

EXAMPLES 11–17

The following all formed clear or slightly turbid formulations with no visible sign of inhomogeneous phase separation after storage at 25° C. for three months. Example 11 illustrates the use of SYNPERONIC L2, an alcohol alkoxylate having a low degree of ethoxylation, as the co-surfactant (component d). Example 12 illustrates the use of an ethoxylated secondary alcohol as the alkoxylated adjuvant (component b). Example 13 illustrates the use of an ethoxylated acetylenic diol as the alkoxylated adjuvant (component b). Example 14 illustrates the use of a block copolymer as the alkoxylated adjuvant (component b). Example 15 illustrates the use of glyceryl monolaurate as the co-surfactant (component d). Example 16 illustrates the use of an ethoxylated laurate as the alkoxylated adjuvant (component b). Example 17 illustrates a composition according to the present invention in which no ionic surfactant (component e) is present.

| Example 11          |           | Example 12          |           |
|---------------------|-----------|---------------------|-----------|
| Glyphosate trimesium | 480 g/l  | Glyphosate trimesium | 480 g/l  |
| AGRIMUL PG2067      | 110 g/l   | AGRIMUL PG2067      | 110 g/l   |
| SYNPERONIC A11      | 110 g/l   | TERGITOL 15-S-9*    | 100 g/l   |
| ARQUAD 16-29        | 69 g/l    | ARQUAD 16-29        | 69 g/l    |
| SYNPERONIC L2*      | 60 g/l    | 2-Ethylhexanol      | 60 g/l    |
| Water               | to 1 liter | Water              | to 1 liter |

*SYNPERONIC L2 is an ethoxylated lauryl alcohol having a mean degree of ethoxylation of 2.
TERGITOL 15-S-9 is an ethoxylated secondary alcohol having a mean degree of ethoxylation of 9. TERGITOL is a trademark of Union Carbide.

| Example 13          |           | Example 14          |           |
|---------------------|-----------|---------------------|-----------|
| Glyphosate trimesium | 480 g/l  | Glyphosate trimesium | 480 g/l  |
| AGRIMUL PG2067      | 110 g/l   | AGRIMUL PG2067      | 110 g/l   |
| SURFYNOL 465*       | 100 g/l   | SYNPERONIC PE P85*  | 100 g/l   |
| ARQUAD 16-29        | 69 g/l    | ARQUAD 16-29        | 69 g/l    |
| 2-Ethylhexanol      | 60 g/l    | 2-Ethylhexanol      | 60 g/l    |
| Water               | to 1 liter | Water              | to 1 liter |

*SURFYNOL 465 is an ethoxylated acetylenic diol with a mean degree of ethoxylation of 10. SURFYNOL is a trademark of Air Products.
SYNPERONIC PE P85 is a block copolymer of ethylene oxide and propylene oxide with a molecular weight of 4650 and containing 50 weight % ethylene oxide.

| Example 15          |           | Example 16          |           |
|---------------------|-----------|---------------------|-----------|
| Glyphosate trimesium | 480 g/l  | Glyphosate trimesium | 480 g/l  |
| AGRIMUL PG 2067     | 110 g/l   | AGRIMUL PG2067      | 110 g/l   |
| SYNPERONIC A11      | 110 g/l   | CITHROL 6ML*        | 110 g/l   |
| ARQUAD 16-29        | 69 g/l    | ARQUAD 16-29        | 69 g/l    |
| CITHROL GML*        | 60 g/l    | 2-Ethylhexanol      | 60 g/l    |
| Water               | to 1 liter | Water              | to 1 liter |

*CITHROL GML is glyceryl monolaurate. CITHROL is a trademark of Croda Chemicals.
CITHROL 6ML is an ethoxylated laurate with a mean degree of ethoxylation of 12.

| Example 17          |           |
|---------------------|-----------|
| Glyphosate trimesium | 480 g/l  |
| AGRIMUL PG2067      | 150 g/l   |
| SYNPERONIC A16      | 120 g/l   |
| Octanol             | 75 g/l    |
| Water               | to 1 liter |

EXAMPLES 18–25

The following all formed clear or slightly turbid formulations with no visible sign of inhomogeneous phase separation after storage at 25° C. for three months. Examples 18 and 19 illustrate the use of pentanol and oleyl alcohol respectively as the co-surfactant. Examples 20 to 22 illustrate the use of alternative alkoxylated adjuvants. Examples 23 to 25 illustrate the use of alternative alkylglycosides.

| Example 18 | | Example 19 | |
|---|---|---|---|
| Glyphosate trimesium | 480 g/l | Glyphosate trimesium | 480 g/l |
| AGRIMUL PG2067 | 110 g/l | AGRIMUL PG2067 | 110 g/l |
| SYNPERONIC A11 | 110 g/l | SYNPERONIC A11 | 110 g/l |
| ARQUAD 16-29 | 69 g/l | ARQUAD 16-29 | 69 g/l |
| Pentanol | 60 g/l | Oleyl alcohol | 60 g/l |
| Water | to 1 liter | Water | to 1 liter |

| Example 20 | | Example 21 | |
|---|---|---|---|
| Glyphosate trimesium | 480 g/l | Glyphosate trimesium | 480 g/l |
| AGRIMUL PG2067 | 110 g/l | AGRIMUL PG2067 | 110 g/l |
| SILWET L77 | 30 g/l | TWEEN 20 | 60 g/l |
| ARQUAD 16-29 | 69 g/l | ARQUAD 16-29 | 69 g/l |
| 2-ethylhexanol | 60 g/l | 2-ethylhexanol | 60 g/l |
| Water | to 1 liter | Water | to 1 liter |

| Example 22 | | Example 23 | |
|---|---|---|---|
| Glyphosate trimesium | 480 g/l | Glyphosate trimesium | 480 g/l |
| AGRIMUL PG2067 | 110 g/l | BEROL AG6202 | 100 g/l |
| SYNPERONIC NP13 | 60 g/l | SYNPERONIC A11 | 100 g/l |
| ARQUAD 16-29 | 69 g/l | ETHOMEEN C12 | 40 g/l |
| 2-ethylhexanol | 60 g/l | Decanol | 40 g/l |
| Water | to 1 liter | Water | to 1 liter |

| Example 24 | | Example 25 | |
|---|---|---|---|
| Glyphosate trimesium | 480 g/l | Glyphosate trimesium | 480 g/l |
| AGRIMUL PG2069 | 150 g/l | AL2042 | 129 g/l |
| SYNPERONIC A11 | 80 g/l | SYNPERONIC A16 | 120 g/l |
| ETHOQUAD C12 | 27 g/l | Octanol | 60 g/l |
| Decanol | 60 g/l | Water | to 1 liter |
| Water | to 1 liter | | |

EXAMPLE 26

Paraquat dichloride containing magnesium sulphate hepta-hydrate (purgative) was formulated according to the present invention as shown below and was stored for 3 months at 25° C. and 40° C. respectively without any visible signs of separation. In contrast the corresponding composition containing no octanol separated within 5 days storage at 25° C. and 40° C. respectively.

| Paraquat dichloride | 276 g/l |
|---|---|
| Magnesium sulphate | 100 g/l |
| AGRIMUL PG2067 | 110 g/l |
| SYNPERONIC PE L44 | 125 g/l |
| ETHOQUAD C12 | 27 g/l |
| Octanol | 40 g/l |
| Water | to 1 liter |

EXAMPLES 27 AND 28

Examples 27 and 28 illustrate the use of further alternative co-surfactants. The compositions given below showed no visible separation after storage for one month at 25° C. In contrast the corresponding composition without the co-surfactant separated after standing at room temperature for a few hours.

| Example 27 | | Example 28 | |
|---|---|---|---|
| Glyphosate trimesium | 480 g/l | Glyphosate trimesium | 480 g/l |
| AGRIMUL PG2067 | 110 g/l | AGRIMUL PG2067 | 110 g/l |
| SYNPERONIC A11 | 110 g/l | SYNPERONIC A11 | 110 g/l |
| ARQUAD 16-29 | 69 g/l | ARQUAD 16-29 | 69 g/l |
| SYNPERONIC OP3 | 60 g/l | SPAN 20 | 50 g/l |
| Water | to 1 liter | Water | to 1 liter |

EXAMPLE 29

The herbicidal activity of glyphosate compositions of the present invention was compared with that of a commercial glyphosate standard. The glyphosate trimesium compositions of Examples 6 to 10 were applied at 240 g/ha in 200 l/ha deionised water. Visual assessment of percentage herbicidal effect was made 25 days after treatment and compared with a commercial glyphosate standard applied at the same rate. The results are presented at mean % control over a range of standard grass species and over a range of standard broad-leaved weeds.

| Treatment | % Control Mean Grasses | % Control Mean Broad Leafed Weeds |
|---|---|---|
| Commercial Standard | 77 | 70 |
| Example 6 | 82 | 67 |
| Example 7 | 81 | 64 |
| Example 8 | 89 | 73 |
| Example 9 | 787 | 69 |
| Example 10 | 90 | 70 |

What is claimed is:

1. An aqueous agrochemical concentrate formulation comprising
    a) an agrochemical electrolyte,
    b) an alkoxylated adjuvant,
    c) an alkylglycoside, and
    d) a co-surfactant which interacts with the alkylglycoside to form a structured aqueous system,
wherein the co-surfactant (d) is
    i) a linear or branched chain aliphatic or aromatic alcohol, or
    ii) an alcohol or ester or alkyl phenol alkoxylate which is an alkoxylated $C_8$–$C_{22}$ alcohol, an alkoxylated $C_8$–$C_{22}$ alkyl phenol or an alkoxylated $C_8$–$C_{22}$ carboxylic acid each containing from 1–3 alkoxy groups provided that the alkoxylated adjuvant (b) contains from 6 to 50 $C_1$–$C_4$ alkoxy groups, or
    iii) a glyceryl alkyl or alkenyl ester,
provided that the concentration of the agrochemical electrolyte is such that the alkoxylated adjuvant would normally undergo uncceptable phase separation in the absence of the co-surfactant which interacts with the alkylglycoside to form a structured aqueous system.

2. A concentrate according to claim 1 wherein the linear or branched chain alcohol (i) is a primary or secondary, linear or branched alkyl or alkenyl alcohol containing from 5 to 20 carbon atoms or is an alkyl-substituted aromatic alcohol containing from 5 to 20 alkyl carbon atoms, or wherein the alcohol or ester or alkyl phenol alkoxylate (ii) is an alkoxylated $C_8$–$C_{22}$ alcohol, an alkoxylated $C_8$–$C_{22}$ alkyl phenol or an alkoxylated $C_8$–$C_{22}$ carboxylic acid each containing from 1–3 ethoxy groups provided that the alkoxylated adjuvant (b) contains from 6 to 50 $C_1$–$C_4$ alkoxy groups, or wherein the glyceryl alkyl or alkenyl ester (iii) is a monoester of a $C_8$–$C_{22}$ carboxylic acid with glycerol.

3. A concentrate according to claim 2 wherein the co-surfactant (d) is pentanol, hexanol, octanol, octan-2-ol, decanol and their branched chain or mixture of branched chain equivalents, oleyl alcohol, 2-ethyl-1hexanol, an ethoxylated lauryl alcohol having a mean degree of ethoxylation of 3, glyceryl monolaurate and sorbitan monolaurate.

4. A concentrate according to claim 1 wherein the agrochemical electrolyte is selected from salts of glyphosate, fomesafen, glufosinate, paraquat and bentazone.

5. A concentrate according to claim 1 wherein the alkoxylated adjutant (b) contains from 6 to 50 $C_1$ to $C_4$ alkoxy groups or is a block copolymer of ethylene oxide and propylene oxide or is a block copolymer obtained by polycondensation of ethylene oxide and propylene oxide on ethylenediamine wherein the block copolymer contains from 30% by weight to 80% by weight of ethylene oxide.

6. A concentrate according to claim 5 wherein the alkoxylated adjuvant (b) is a non-ionic adjuvant which is an ethoxylated primary or secondary linear or branched alcohol containing an average of from 8 to 22 carbon atoms in the (linear or branched) alkyl moiety, an ethoxylated carboxylic acid containing an average of from 8 to 22 carbon atoms in the (linear or branched) alkyl moiety, an ethoxylated alkyl aryl wherein the alkyl group contains an average of from 5 to 20 carbon atoms, an ethoxylated sorbitan ester wherein the ester group contains from 8 to 22 carbon atoms, an ethoxylated acetylenic diol containing an average of from 8 to 22 carbon atoms in the (linear or branched) alkyl moiety, ethoxylated trisiloxanes, ethoxylated amides and the propoxylated or ethoxylated and propoxylated analogues of all the aforesaid ethoxylated non-ionic adjuvants.

7. A concentrate according to claim 1 wherein the composition additionally contains a cationic surfactant having at least one linear or branched long chain alkyl or alkenyl or alkyl aryl substituent containing from 8 to 20 alkyl or alkenyl carbon atoms and a mean ethylene oxide content of from 0 to 20 which is an optionally ethoxylated amine, quaternary ammonium salt or amine oxide or wherein the composition additionally contains an anionic surfactant having at least one long chain alkyl or alkenyl substituent containing from 8 to 20 carbon atoms which is an alkyl sulphate, alkyl carboxylate, alkyl sulphosuccinate, alkyl phosphate or alkylbenzene sulphonate and derivatives thereof.

8. A concentrate according to claim 7 wherein the proportion of additional ionic surfactant is from 0 parts by weight to 1 parts by weight ionic surfactant per 1 part alkylglycoside.

9. A concentrate according to claim 7 wherein the proportion by weight of the total of the alkylglycoside, alkoxylated adjuvant and additional ionic surfactant, if used, to the agrochemical electrolyte is from 2:1 to 1:5.

10. A concentrate according to claim 1 wherein the proportion of the alkoxylated adjuvant is from 8 parts by weight alkoxylated adjuvant per 1 part by weight alkyl glycoside to 1 part by weight alkoxylated adjuvant per 8 parts by weight alkylglycoside.

11. A concentrate according to claim 1 wherein the proportion of the co-surfactant is preferably from 0.1 parts by weight to 1 part by weight per 1 part by weight of alkylglycoside.

12. A process for severely damaging or killing unwanted plants which comprises applying to the plants a herbicidally effective amount of a composition according to claim 1 wherein the agrochemical electrolyte is a herbicide.

13. A process for the preparation of a composition according to claim 7 wherein the agrochemical electrolyte, the alkylglycoside and the alkoxylated adjuvant are dissolved or dispersed in water with the further ionic surfactant, if used, and thereafter the co-surfactant is added and interacts with the alkylglycoside to form a structured system.

* * * * *